United States Patent
Field et al.

(10) Patent No.: US 6,673,291 B1
(45) Date of Patent: Jan. 6, 2004

(54) METHODS OF MANUFACTURING MEDICO-SURGICAL TUBES

(75) Inventors: Stephen James Field, Canterbury (GB); Kester Julian Batchelor, Burnham-on-Sea (GB)

(73) Assignee: Smiths Group PLC (GB)

( * ) Notice: Subject to any disclaimer, the term of this patent is extended or adjusted under 35 U.S.C. 154(b) by 244 days.

(21) Appl. No.: 09/644,977

(22) Filed: Aug. 24, 2000

Related U.S. Application Data

(62) Division of application No. 09/292,983, filed on Apr. 20, 1999.

(30) Foreign Application Priority Data

May 1, 1998 (GB) ............................................. 9809246

(51) Int. Cl.⁷ .............................................. B29C 47/06
(52) U.S. Cl. ...................... 264/139; 264/145; 264/154; 264/211.12; 264/209.3
(58) Field of Search ................................. 264/139, 145, 264/154, 155, 162, 171.26, 173.16, 173.19, 174.11, 210.1, 210.2, 211.12, 209.3

(56) References Cited

U.S. PATENT DOCUMENTS

| | | | |
|---|---|---|---|
| 3,508,554 A | * | 4/1970 | Sheridan ................. 264/209.7 |
| 3,924,632 A | * | 12/1975 | Cook ......................... 604/527 |
| 4,211,741 A | * | 7/1980 | Ostoich .................. 264/171.26 |
| 4,250,072 A | * | 2/1981 | Flynn ......................... 524/288 |
| 4,330,497 A | * | 5/1982 | Agdanowski ................ 264/139 |
| 4,385,635 A | | 5/1983 | Ruiz |
| 4,596,563 A | * | 6/1986 | Pande ......................... 604/264 |
| 4,636,346 A | | 1/1987 | Gold et al. |
| 4,753,765 A | | 6/1988 | Pande |
| 4,775,371 A | | 10/1988 | Mueller, Jr. |
| 4,904,431 A | * | 2/1990 | O'Maleki .................... 264/139 |
| 5,348,536 A | | 9/1994 | Young et al. |
| 5,499,980 A | * | 3/1996 | Euteneuer .................... 264/317 |
| 5,558,737 A | | 9/1996 | Brown et al. |
| 5,888,436 A | * | 3/1999 | Keith et al. .................. 264/103 |
| 5,976,120 A | * | 11/1999 | Chow et al. ................. 604/525 |
| 6,224,803 B1 | * | 5/2001 | Tiernan ....................... 264/166 |

FOREIGN PATENT DOCUMENTS

| | | | |
|---|---|---|---|
| EP | 0 597 341 | 5/1994 | |
| EP | 530201 B1 | * 8/1994 | .......... A61M/25/00 |
| EP | 0 827 758 | 3/1998 | |
| WO | WO 94/01160 | 1/1994 | |

* cited by examiner

Primary Examiner—Mark Eashoo
Assistant Examiner—Geoffrey P. Shipsides
(74) Attorney, Agent, or Firm—Connolly, Bove, Lodge & Hutz LLP

(57) ABSTRACT

An epidural catheter with a soft tip is formed by extruding a two-layer tube where the inner layer is stiffer than the outer layer. The inner layer is then removed, such as by machining, from a short length at the tip, which is subsequently end-formed closed and a side opening cut into it.

11 Claims, 2 Drawing Sheets ial. The wall 10 has
METHODS OF MANUFACTURING MEDICO-SURGICAL TUBES

RELATED APPLICATION

The present application is a divisional of U.S. patent application Ser. No. 09/292,983, filed Apr. 20, 1999.

FIELD OF THE INVENTION

This invention relates to medico-surgical tubes and methods of manufacture.

The invention is more particularly concerned with tubes with a soft tip, and with methods of manufacture of such tubes.

BACKGROUND OF THE INVENTION

It is often desirable for medico-surgical tubes, or catheters, to have a soft tip, so as to reduce trauma caused when the tip contacts patient tissue. In epidural catheters, a soft tip reduces the risk that the catheter will damage the dura. Various arrangements have been proposed for providing a soft tip, such as by attaching or moulding onto the shaft of the catheter a separate component of a softer material. Such an arrangement is not entirely satisfactory because a separate assembly operation is needed to form the tip, leading to increased manufacturing expense. Also, there is always some risk that a separate component might become detached from the body of the catheter. Other arrangements in which the rear part of the catheter is reinforced can also be difficult to make by automated assembly, thereby making the catheter relatively expensive. GB9906349 describes a catheter with a soft tip formed by extruding a tube with an inner layer of stiffer material, which is periodically interrupted to provide more flexible regions. In WO 94/01160 there is described an epidural catheter where an inner tube is preformed and then an outer tube is provided around it extending beyond the inner tube to form a less stiff region.

BRIEF SUMMARY OF THE INVENTION

It is an object of the present invention to provide an alternative medico-surgical tube and method of manufacture of a such a tube.

According to one aspect of the present invention there is provided a medico-surgical tube having an inner layer and an outer layer, a part at least of the inner layer being removed from one end of tube such as to reduce the stiffness of the tube at the one end.

The tube may have an interlayer, such as of polyethylene, between the inner and outer layers preventing bonding between the inner and outer layers and enabling the part of the inner layer to be pulled from the one end of the tube. The tube is preferably closed at the one end and has a side opening towards the one end. The inner layer is preferably stiffer than the outer layer.

According to another aspect of the present invention there is provided a method of making a medico-surgical tube including the steps of forming a tubular member with an inner and outer layer, and subsequently removing a part at least of the inner layer along a region at one end of the tube such as to reduce the stiffness of the tube along the region.

The part of the inner layer may be removed by machining away the part of the inner layer along the region. The part of the inner layer may be machined away using a machine having a rotating milling head with a milling surface on an end face. Alternatively, the part of the inner layer may be removed by cutting away the part from the remainder of the inner layer and pulling it out of the tube. The part of the inner layer may be cut away using a machine having a rotating spindle carrying a radially-extending knife blade. Preferably the tube has an interlayer, such as of polyethylene, between the inner and outer layers preventing bonding between the inner and outer layers. The inner layer may be of a stiffer material than the outer layer. The outer layer is preferably end formed after removal of the part of the inner layer to close the one end of the tube, a side opening being formed in the tube towards the one end.

According to a further aspect of the present invention there is provided a medico-surgical tube made by a method according to the above other aspect of the invention.

According to a fourth aspect of the present invention there is provided a machine for use in the method according to the above other aspect of the invention.

An epidural catheter and a method of making an epidural catheter according to the present invention, will now be described, by way of example, with reference to the accompanying drawings.

DETAILED DESCRIPTION OF THE PREFERRED EMBODIMENTS

Figure 1:
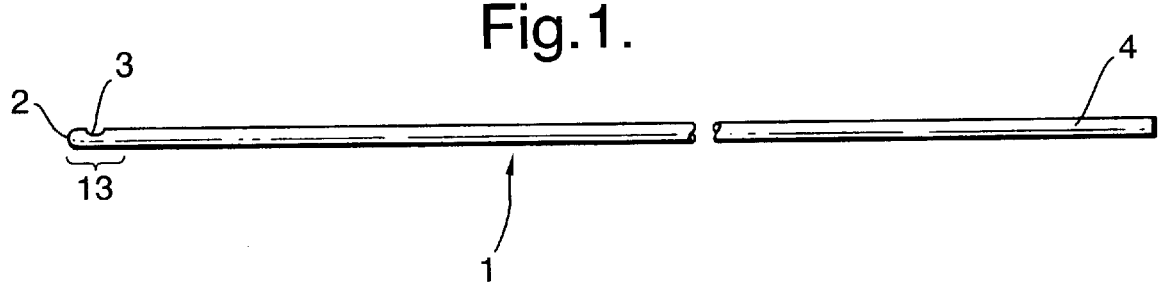
FIG. 1 is a side elevation view of the catheter.

With reference first to FIG. 1, the catheter 1 is about 75–100 cm long with a rounded tip at its patient end 2 and a side opening 3. The machine end 4 of the catheter 1 is open and cut square for attachment to a conventional epidural connector, not shown.

Figure 2:
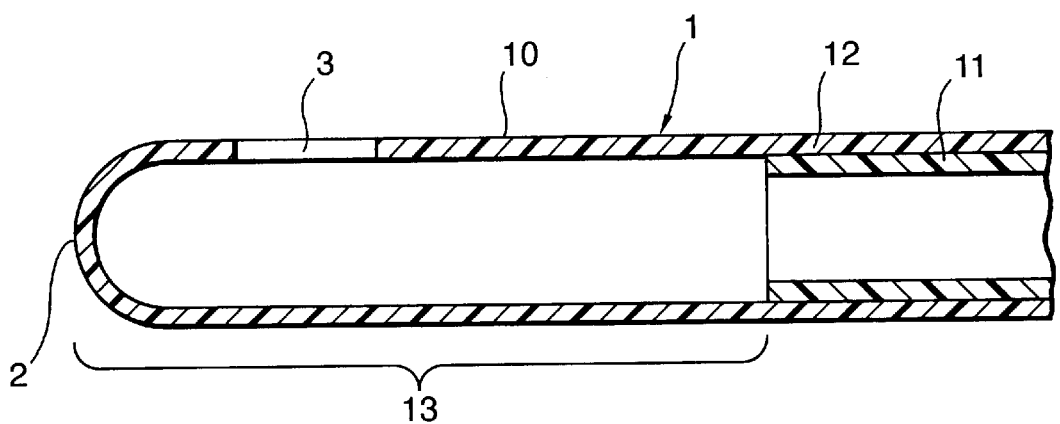
FIG. 2 is an enlarged cross-sectional side elevation view of the patient end of the catheter.

Referring now also to FIG. 2, the wall 10 of the catheter 1 is extruded from a thermoplastics material. The wall 10 has an inner layer 11 of nylon and an outer layer 12 of polyurethane, the nylon being stiffer than the polyurethane. Alternatively, both layers 11 and 12 may be of the same polymer, such as PVC, but with differing amounts of plasticizer so that the inner layer is stiffer. Towards the patient end 2 of the catheter 1, there is a region 13 about 2 cm long where the inner layer 11 has been removed, thereby making this more flexible than the remainder of the catheter 1, and making the tip 2 relatively soft. This reduces the risk of damage to the dura and enables the forward end of the catheter 1 to bend more easily to conform to the shape of the epidural space with a reduced risk of kinking. Because the inner layer 11 is stiffer than the outer layer 12, it can be relatively thin and still provide sufficient rigidity to the main part of the catheter. This ensures that the internal diameter of the catheter 1 is kept as large as possible.

Figure 3:
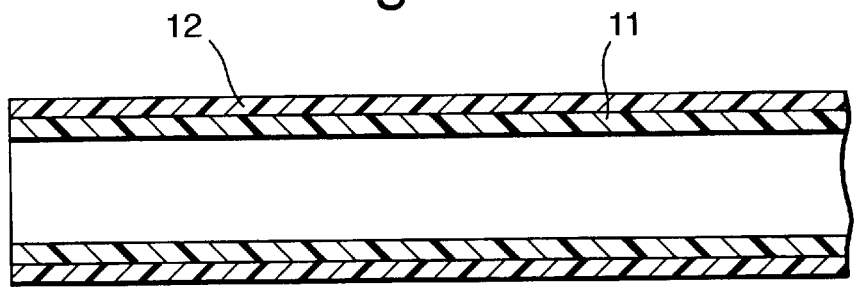
FIGS. 3 and 4 are enlarged cross-sectional side elevation views showing stages in a method of manufacture of the catheter.
Figure 4:
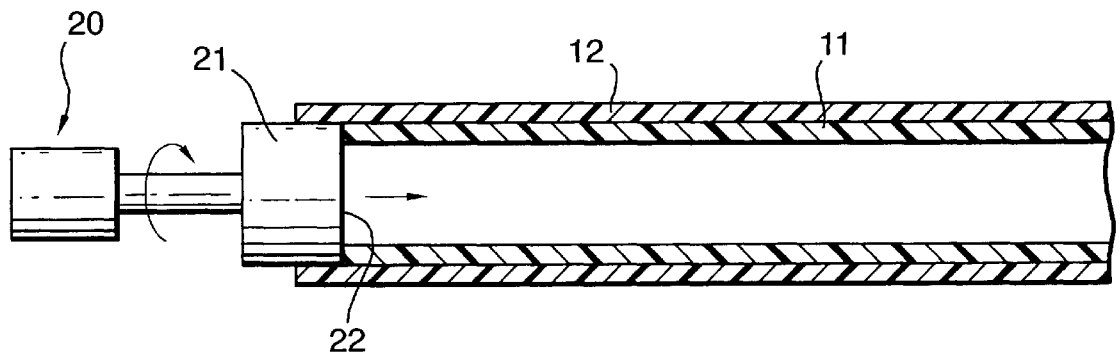

The inner layer 11 can be removed from the tip of the catheter in various ways, such as illustrated in FIGS. 3 and 4. FIG. 3 shows tubing as it emerges from a co-extruder, having an inner layer 11 extending along its entire length. The tubing is then cut into lengths and the inner layer 11 is subsequently removed by machining it away, such as with a milling machine 20 of the kind shown in FIG. 4. The machine 20 has a milling head 21 of cylindrical shape with a milling surface formed on its front face 22. The diameter of the head 21 is equal to the external diameter of the inner layer 11. The milling head 21 is rotated about its axis and is pushed axially into the tubing so as to cut away the inner layer 11 and to leave the outer layer 12. The head 21 is pushed in until the inner layer 11 has been machined away along the region 13. The machine 20 is then removed, the swarf is flushed from the tube and the tube is end formed in a conventional manner, such as by means of a heated mould, to close and round the end. The side eye 3 can be formed at any time.

It is not essential to remove the entire thickness of the inner layer 11 since some reduction in stiffness can be achieved by removing only an inner part of the thickness of the layer.

Figure 5:
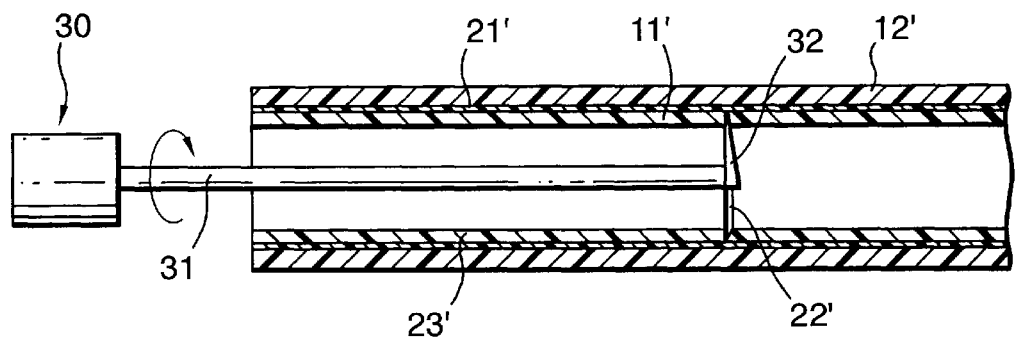
FIGS. 5 and 6 are an enlarged cross-sectional side elevation views showing stages in an alternative method of manufacture of the catheter.
Figure 6:
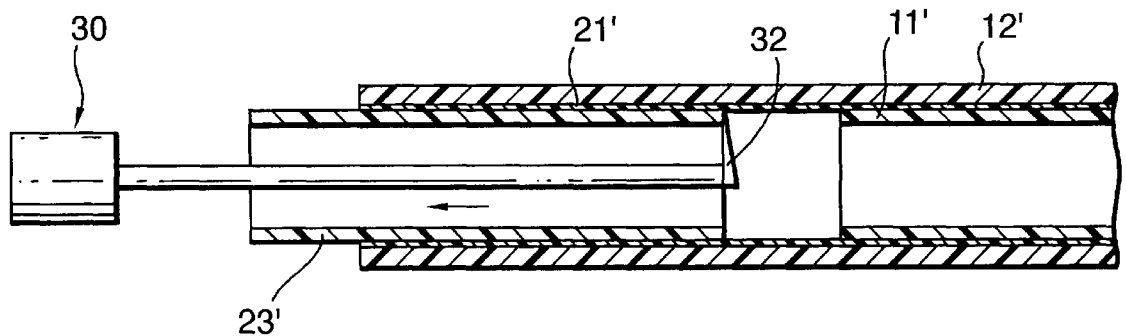

An alternative way of removing the inner layer 11' is shown in FIGS. 5 and 6. In this method, the tubing is extruded with an additional interlayer 21' of polyethylene between the outer layer 12' and the inner layer 11', which serves to prevent bonding between the inner and outer layers. After cutting into appropriate lengths, a cutting machine 30 is used to remove the inner layer 11'. The cutting machine 30 has a rotatable spindle 31 carrying a radially-extending knife blade 32 at one end. The blade 32 is inserted, while stationary, into the end of the tube to a depth equal to that of the region 13 from which the inner layer 11' is to be removed. The machine 30 then rotates and centers the spindle 31 within the tube. The length of the knife blade 32 is selected so that its tip traces a circle of diameter equal to the external diameter of the inner layer 11' and thereby produces a circular cut 22' through the inner layer without penetrating the outer layer 12'. The spindle 31 and blade 32 are then stopped rotating and are pulled out of the tube, as shown in FIG. 6, with the blade pulling out the section 23' of the inner layer 11' forwardly of the cut 22', which has been separated from the remainder of the inner layer. The interlayer 21' ensures that this section 23' of the inner layer 11' can be slid relative to the outer layer 12'. It is not important whether the knife blade 32 cuts through the interlayer 21' and whether this is removed with the section 23' of the inner layer 11', or whether it remains within the outer layer 12'. Alternatively, a separate tool could be used to remove the section 23'. The end of the tube is then formed in the manner described above. This arrangement has the advantage that less or no swarf is produced.

The method of making the catheter 1 enables a soft patient end tip 2 to be provided without the need for subsequent assembly operations.

It will be appreciated that the invention is not confined to epidural catheters but could be used to provide a tip of reduced stiffness to other tubes such as endotracheal tubes. The catheter could be reinforced such as by incorporating a helical reinforcing element, or a braid into the outer layer. A lumen could be formed along the outer layer for various conventional purposes. The tip could be open or closed.

What we claim is:

1. A method of making a medico-surgical tube comprising:
    forming an inner tubular member;
    forming an outer tubular member coaxial with said inner tubular member; and subsequently
    mechanically removing at least a part of said inner tubular member from said outer tubular member along a region at one end of said medico-surgical tube such as to reduce the stiffness of said medico-surgical tube along said region.

2. A method according to claim 1, wherein said part of said inner tubular member is removed by machining away said part of said inner tubular member along said region.

3. A method according to claim 2, wherein said part of said inner tubular member is machined away using a machine having a rotating milling head, said milling head having a milling surface on an end face.

4. A method according to claim 1, wherein said part of said inner tubular member is removed by cutting away said part from a remainder of said inner tubular member and pulling said part out of said medico-surgical tube.

5. A method according to claim 4, wherein said part of said inner tubular member is cut away using a machine having a rotating spindle carrying a radially-extending knife blade.

6. A method according to claim 4, wherein said medico-surgical tube has an interlayer tubular member between said inner and outer tubular members preventing bonding between said inner and outer tubular members.

7. A method according to claim 6, wherein said interlayer tubular member comprises polyethylene.

8. A method according to claim 1, including end forming said outer tubular member after removing said part of said inner tubular member so as to close said one end of said medico-surgical tube, and forming a side opening in said medico-surgical tube towards said one end.

9. A method of forming a medico-surgical tube comprising:
    forming an inner tubular member;
    forming an outer tubular member coaxial with said inner tubular member; subsequently
    mechanically removing a part at least of said inner tubular member from said outer tubular member along a length at one end of said medico-surgical tube;
    closing said tube at said one end to leave a region at said one end from which said part has been removed that is less stiff than the remainder of said medico-surgical tube; and
    forming a side opening in said medico-surgical tube towards said one end.

10. A method of forming a medico-surgical comprising:
    forming an inner tubular member;
    forming an outer tubular member coaxial with said inner tubular member;
    machining away a part at least of the thickness of the inner tubular member from one end of said medico-surgical tube to remove a part at least of said inner tubular member from a predetermined length of the medico-surgical tube at said one end;
    closing said tube at said one end to leave a region at said one end that is less stiff than the remainder of the medico-surgical tube; and
    forming a side opening in said medico-surgical tube towards said one end.

11. A method of forming a medico-surgical comprising:
    forming a continuous inner tubular member;
    forming a tubular interlayer member coaxial with said inner tubular member;
    forming a continuous outer tubular member coaxial with said inner tubular member and said tubular interlayer member, wherein said interlayer member prevents bonding between said inner and outer tubular members;
    inserting a cutting machine into one end of said medico-surgical tube;
    cutting a circular cut with said cutting machine through the complete thickness of said inner tubular member to separate a length of said inner tubular member from the remainder of said inner tubular member;

pulling out said separated length of the inner tubular member from said medico-surgical tube;

closing said medico-surgical tube at said one end to leave a region of said medico-surgical tube without an inner tubular member that is less stiff than the remainder of said medico-surgical tube; and forming a side opening in said medico-surgical tube towards said one end.

* * * * *